(12) United States Patent  (10) Patent No.: US 7,373,721 B2
Bergamasco et al.  (45) Date of Patent: May 20, 2008

(54) GONIOMETRIC SENSOR

(76) Inventors: Massimo Bergamasco, V. Don Minzoni, 144 56011 Castelmaggiore, Calci (PI) (IT); Fabio Salsedo, Viale Umberto Primo, 10004100 Latina (IT); Guenther Nino Ullrich, Viale Trieste, 354100 Massa (IT); Paolo Villella, Via Gentileschi, 856123 Pisa (IT)

( * ) Notice: Subject to any disclaimer, the term of this patent is extended or adjusted under 35 U.S.C. 154(b) by 0 days.

(21) Appl. No.: 10/540,916

(22) PCT Filed: Dec. 30, 2002

(86) PCT No.: PCT/IB02/05665

§ 371 (c)(1),
(2), (4) Date: Jul. 21, 2005

(87) PCT Pub. No.: WO2004/059249

PCT Pub. Date: Jul. 15, 2004

(65) Prior Publication Data

US 2006/0015191 A1    Jan. 19, 2006

(51) Int. Cl.
*G01B 3/56*  (2006.01)
(52) U.S. Cl. ...................................... 33/1 N
(58) Field of Classification Search .................. 73/538; 33/1 N
See application file for complete search history.

(56) References Cited

U.S. PATENT DOCUMENTS

| | | | | |
|---|---|---|---|---|
| 4,570,354 A | * | 2/1986 | Hindes | 33/534 |
| 4,606,696 A | * | 8/1986 | Slocum | 414/744.2 |
| 4,940,063 A | * | 7/1990 | Challis | 600/587 |
| 4,972,073 A | * | 11/1990 | Lessing | 250/227.16 |
| 5,044,084 A | * | 9/1991 | Pfeiffer et al. | 33/1 PT |
| 5,610,528 A | * | 3/1997 | Neely et al. | 324/660 |
| 5,633,494 A | * | 5/1997 | Danisch | 250/227.16 |
| 5,772,610 A | | 6/1998 | McGorry et al. | |
| 6,117,091 A | | 9/2000 | Young et al. | |
| 6,651,352 B2 | * | 11/2003 | McGorry et al. | 33/512 |
| 2003/0154613 A1 | * | 8/2003 | Hodac | 33/534 |

FOREIGN PATENT DOCUMENTS

| | | | |
|---|---|---|---|
| JP | 58015108 | | 4/1983 |
| JP | 64-41803 | * | 2/1989 |
| WO | 9807368 | | 2/1998 |

* cited by examiner

*Primary Examiner*—Robert Raevis
(74) *Attorney, Agent, or Firm*—Dennison, Shultz & MacDonald

(57) ABSTRACT

A goniometric sensor (1) for measuring the relative rotation of two objects (20,25) comprising a flexible elongated element (2) whose respective ends are connected to the two objects (20, 25) and during whose bending the length variation ΔL is determined of one of the lines (15) not located at the neutral axis (10). This length variation ΔL is directly proportional to the relative rotation (α) between the two bodies (20, 25) multiplied for the eccentricity (e) of the line (15) with respect to the neutral axis (10). Therefore, it is possible to determine easily the relative rotation (α) by knowing the length L and the eccentricity (e) with respect to the neutral axis 10, and measuring the length variation ΔL of the line, for example by measuring the movement of the end of a cable located in a hole that contains the line.

13 Claims, 4 Drawing Sheets

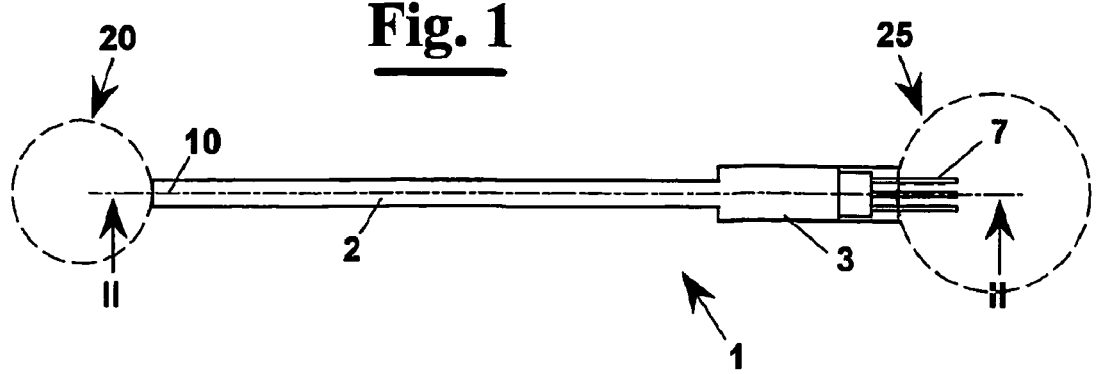
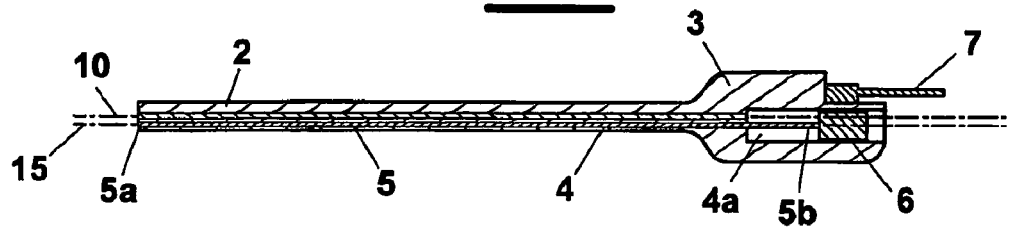
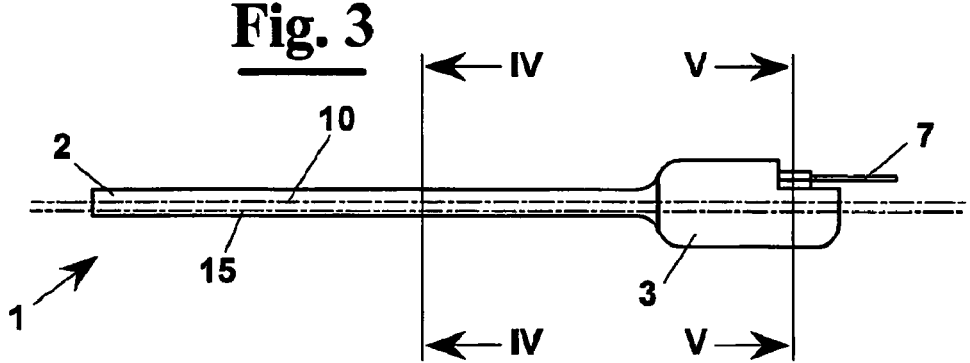
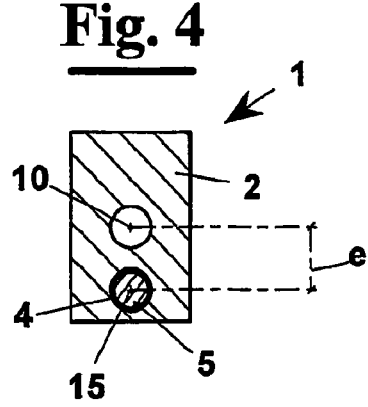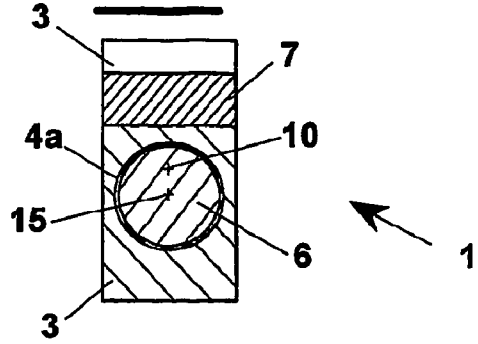

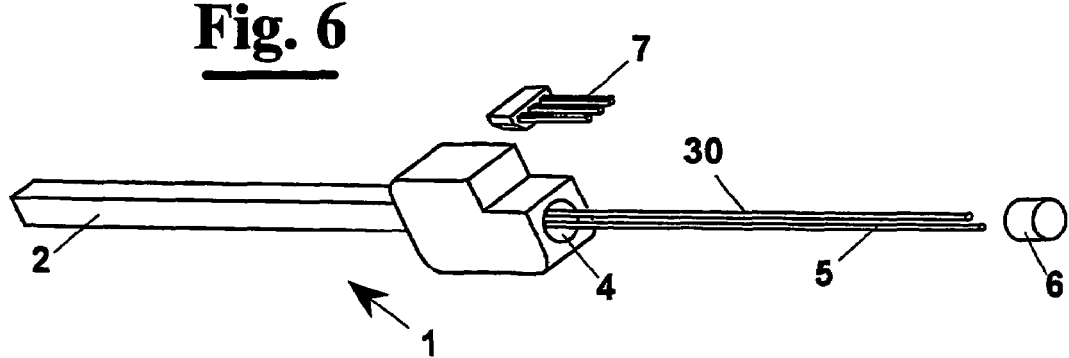
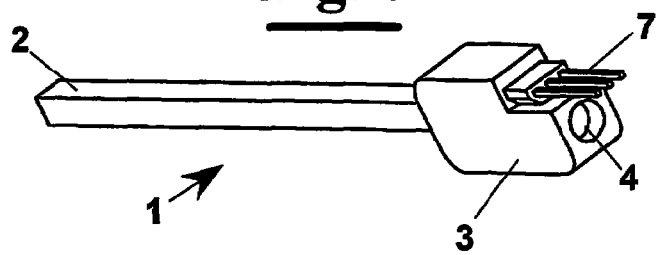
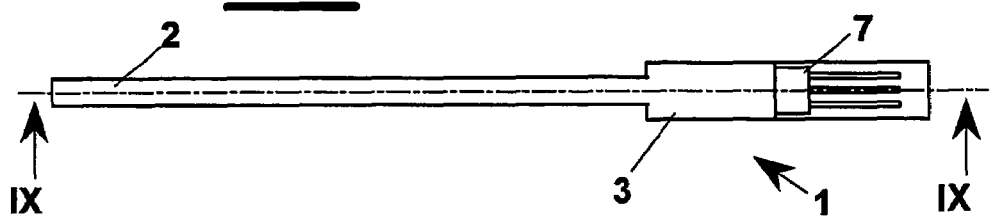
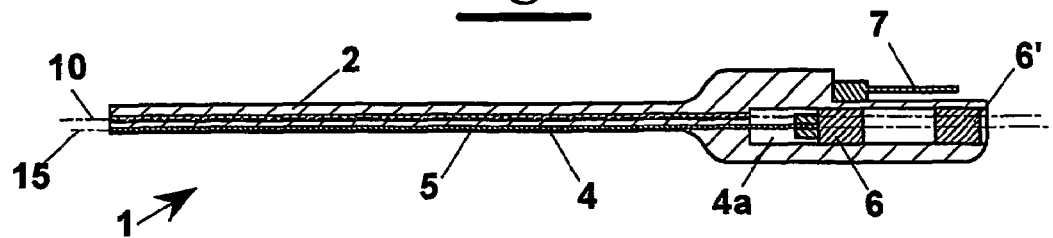

GONIOMETRIC SENSOR

This application is a filing under 35 USC 371 of PCT/IB2002/005665, Dec. 30, 2002.

FIELD OF THE INVENTION

The present invention generally relates to a device for determining the angle of rotation of an object moving in space with respect to a reference object.

In particular, the invention relates to a device for determining the relative angular position of two bodies moving in space with respect to each other.

BACKGROUND OF THE INVENTION

Various electro-mechanical sensors exist used for measuring angular position between two bodies rotating with respect to each other. However, such sensors usually measure the relative angular position of bodies mechanically connected by rigid joints, for example the steering wheel and the transmission shaft of a car.

The nature of the sensors mentioned above remarkably limits the applicability in special fields such as, for example, virtual reality or the design of artificial prosthesis in medicine.

In particular, such sensors are not suitable in fields that, owing to technological progress, have recently captured the attention of many researchers, i.e. acquisition and analysis of movement of human body parts. By using absolute position data of single points of the human body or angular relative positions between two adjacent limbs, a digital model of the human body can be created.

The known sensors suitable for this particular fields depend on the type of application and on the limbs that have to be monitored.

In particular, the limbs with greater volume, such as arms and legs of a human, have few degrees of freedom and the devices used for detecting their motion usually have higher weight and encumbrance and require a higher rate of precision. The limbs with smaller volume, instead, such as the fingers of the hand that have a higher number of degrees of freedom, cannot be monitored with heavy and bulky devices and require less precision.

The known sensors used for tracking the motion of the limbs of the human body are usually of magnetic, optical, ultrasonic or mechanical nature.

Among them, two main categories of sensors exist:
1) sensors that do not require a mechanical connection between the reference object and the object to be monitored.
2) sensors that require a mechanical connection between the reference object and the object to be monitored.

To the first category the following belong:

Magnetic sensors, which require one or more transmitters for creating a magnetic field in a determined workspace. In particular, they have high costs and have the further drawback of being particularly sensitive to the presence of metal that can distort the magnetic field.

Optical sensors, which require optical markers, either active or reflective, whose light is captured allowing a computer to calculate its position. Usually, the optical devices are less bulky than the magnetic, but their functionality can be affected by parts of the body that cross accidentally the path of the light. Another drawback of the optical devices are high costs and the need for a post-processing of the measured data, as well as the long set up time for calibrating the measuring equipment.

To the second category the following belong:

Sensors of mechanical type, based on strain gauges embedded in a flexible support structure, providing the angle of rotation of the sensor-support assembly. Their performances are high but they have reliability problems and a high cost;

Sensors based on optical lines, which measure the variation of intensity of a light beam projected in an optical line. This measure reveals the angle of rotation of the sensor support. Such sensors have a relatively low cost but have reliability problems and low measuring precision.

SUMMARY OF THE INVENTION

It is therefore object of the present invention to provide a goniometric sensor for determining the relative angular position of two objects.

It is another object of the present invention to provide a goniometric sensor that is structurally simple and cost effective.

It is a further objective of the present invention to provide a goniometric sensor capable of overcoming the drawbacks of the devices of prior art.

These and other objectives are accomplished by the goniometric sensor, according to the present invention, for measuring the relative rotation of a first object and a second object whose characteristic is that it comprises:
- a flexible elongated element that extends between said first and said second object, said element having a neutral axis, which does not change its own length when bending, and at least one line located apart from said neutral axis and that extends from said first to said second object;
- means for measuring the length variation of said line as the relative rotation varies between said first and said second object, said relative rotation being proportional to said length variation.

Preferably, the bending of said flexible elongated element is carried out in a predetermined plane.

Advantageously, said or each line is associated to a channel that runs the flexible elongated element along said line, in said channel a medium being present suitable for transmitting a signal to said means for measuring said length variation.

In particular, the medium suitable for transmitting said signal is a cable connected to a first point of the channel and wherein said means for measuring record the movement of the cable at a second point of the channel.

Advantageously, said cable has one end connected to an end of the channel and has the other end freely moving, whereby the sensing device measures the movement of the free moving end with respect to the channel.

Advantageously, said means for measuring the length variation of the line are chosen among: Hall effect sensors, optical sensors, magnetic induction sensors, piezoelectric sensors, etc.

According to a possible alternative embodiment, the flexible elongated element has at least one channel closed at the ends that is eccentric with respect to the neutral axis and in which a certain amount of a compressible fluid is contained, for example air, at a measured pressure. A bending action of the flexible elongated element causes a pressure variation of the fluid in the channel, detected by means for measuring the pressure variation and converted into a measure of the length variation proportional to the detected pressure variation.

In a further embodiment, the eccentric tubular channel is closed at one end and is filled with an amount of incompressible fluid, a position reference element being slidingly arranged at the other end. In this case, the bending of the flexible elongated element causes a variation of the distribution of the incompressible fluid in the tubular channel and then a movement of the reference element, which is detected by said means for measuring the variation of the length.

According to a particular aspect of the invention, the goniometric sensor as above described can be advantageously mounted on a data glove. In particular, at each finger of the glove at least one goniometric sensor is arranged according to the invention, having an end constrained to the back of the hand in order to extend for at least one portion of the finger same. In this way, it is possible to measure relative angular movements of the different fingers of the glove. The goniometric data glove thus obtained can have applications, for example, in the field of virtual reality, in the medical field, etc. For example, two or three goniometric sensors can be used for each finger of the hand for measuring the flexo-extension of each phalanx, and a goniometric sensor rotated of 90° about its own axis can be used for measuring the ab-adduction of the fingers with respect to the hand.

Another particular aspect of the invention relates to a device for measuring the rotation of the wrist of an arm comprising at least one goniometric sensor as above described. In particular, said or each goniometric sensor is arranged with an end integral to the wrist and with the other end constrained to a second point of the arm that during the rotation of the wrist remains substantially fixed, for example the elbow. Therefore, the goniometric sensor measures the rotation of the wrist with respect to the second point of the arm. Furthermore, two sensors can be used at the wrist, which operate in two planes orthogonal to each other and that contain the axis of the forearm. This solution is suitable for the acquisition of the data relating respectively to the flexo-extension and the ab/adduction of the hand with respect to the forearm.

A further particular aspect of the invention provides a plurality of goniometric sensors as above described arranged in series along a rope that connects an object in movement to a reference point. This way, a device is obtained for fully localizing and monitoring the object position, by integrating the results of each single goniometric sensor using a computing unit, assuming a constant curvature of the rope in each portion including a single sensor.

BRIEF DESCRIPTION OF THE DRAWINGS

Further features and the advantages of the goniometric sensor according to the present invention will be made clearer with the following description of an embodiment thereof, exemplifying but not limitative, with reference to the attached drawings, wherein:

FIG. 1 shows a top plan view of a goniometric sensor according to the invention;

FIG. 2 shows a longitudinal sectional view according to arrows II-II of the goniometric sensor of FIG. 1;

FIG. 3 shows a side view of the goniometric sensor of FIG. 1;

FIGS. 4 and 5 show a cross sectional view of the goniometric sensor of FIG. 1 respectively according to arrows IV-IV and V-V;

FIGS. 6 and 7 show the goniometric sensor of FIG. 1 in a perspective view respectively exploded and assembled;

FIG. 8 shows a top plan view of an alternative embodiment of the sensor of FIG. 1;

FIG. 9 shows a longitudinal sectional view according to arrows IX-IX of the goniometric sensor of FIG. 8;

DESCRIPTION OF A PREFERRED EMBODIMENT

Figure 10:
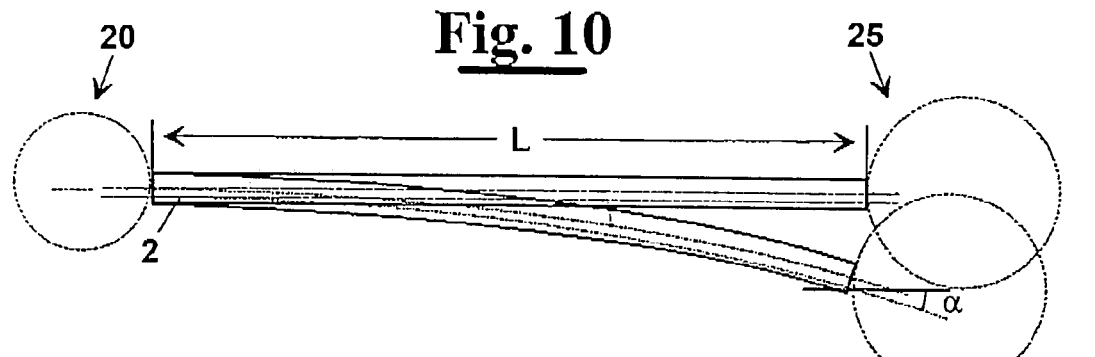
FIG. 10 shows diagrammatically the working principle of the goniometric sensor of FIG. 1.

With reference to FIGS. 1 and 2, a sensor for goniometric measures 1, according to the present invention, measures the relative rotation of two bodies 20 and 25, symbolically indicated with circles in FIG. 1.

In particular, sensor 1 comprises a flexible elongated element 2 whose respective ends are connected to bodies 20 and 25. Goniometric sensor 1 has an axis of symmetry 10 that is the same of element 2. At the bending of element 2, the axis 10 becomes also neutral axis, i.e. it has lines that do not lengthen or shorten when bending. Furthermore, numeral 15 indicates a generic line that is eccentric with respect to the neutral axis.

When bodies 20 and 25 rotate with respect to each other, flexible elongated element 2 is subject to a bending that produces a length variation of the lines different from the neutral axis 10. In particular, a line coincident to eccentric line 15 is subject to a length variation $\Delta L$ (FIG. 10). It must be noted that the neutral axis changes according to the beam geometry, and then it does not always coincide with the axis of symmetry.

Such length variation $\Delta L$ is directly proportional to the relative rotation between the two bodies 20 and 25, and in particular it is proportional to the product of the angle to measure ($\alpha$) and of the eccentricity (e) with respect to the neutral axis. Therefore, it is possible to determine easily the relative rotation $\alpha$ by knowing the eccentricity of the cable with respect to the neutral axis 10 and measuring the length variation $\Delta L$.

It must be noted that if a rotation according to an angle $\alpha$ of the flexible elongated element 2 causes a lengthening $\Delta L$ of line 15, an opposite rotation equal to $-\alpha$ of the flexible elongated element 2 causes a shortening $-\Delta L$ of the same line 15. This is very advantageous in order to double the range of measurable angles.

In a first embodiment of the invention (FIGS. 2-7) the length variation of line 15 is determined by a sensor 7, for example a Hall effect sensor, which detects the movement of the end of a cable 5 located in a channel 4 made at the end of element 2.

In the case shown in the figures, cable 5 has an end 5a connected to an end of elongated element 2 and the other end 5b connected to a magnet 6 sliding in an enlarged portion 4a of channel 4. Therefore, a relative angular movement of the two bodies 20 and 25 causes the above described variation ΔL of the length of line 15 that forces the cable 5 to slide in channel 4 and then causes magnet 6 to slide in the enlarged portion 4a of a corresponding portion. The movement of magnet 6, and then the variation ΔL of the length of line 15 is detected by sensor 7 located near magnet 6 same and then encoded into a measure of the relative rotation α, exploiting the above cited equation between eccentricity, angle and lengthening.

As shown in FIG. 6 in an exploded view, at the neutral axis 10 of goniometric sensor 1 a stiffening element 30 can be located, in particular if the elongated element should have a high axial stiffness.

In FIGS. 7 to 9 an alternative embodiment is shown of goniometric sensor 1, wherein in the enlarged portion 4a of channel 4 in addition to magnet 6 a second magnet 6' is arranged having mainly the function of keeping stretched cable 5 attracting magnet 6 when detecting the variation of its length by sensor 7.

Alternatively to FIGS. 1 to 9 above described, in which sensor of presence 7 is shown arranged in a plane parallel to channel 4, the sensor of presence can be arranged, according to an embodiment not shown, in a plane orthogonal to the axis of channel 4 same.

Elongated element 2 shown in FIGS. 1-9 can be made, advantageously, in two different parts: a first elongated portion 2 and a head 3 to it releasably engageable. On releasable head 3 sensor 7 is mounted and a channel is made, co-axial to channel 4 of elongated element 2, in which sliding magnet 6 is arranged.

Figure 11:
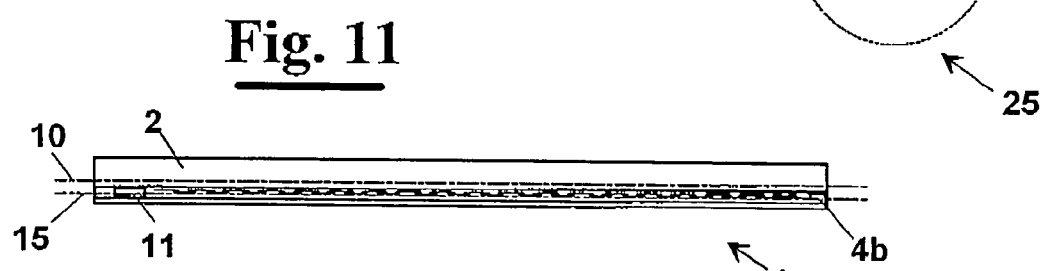
FIGS. 11 and 12 show diagrammatically a further alternative embodiment of the goniometric sensor of FIG. 1.
Figure 12:
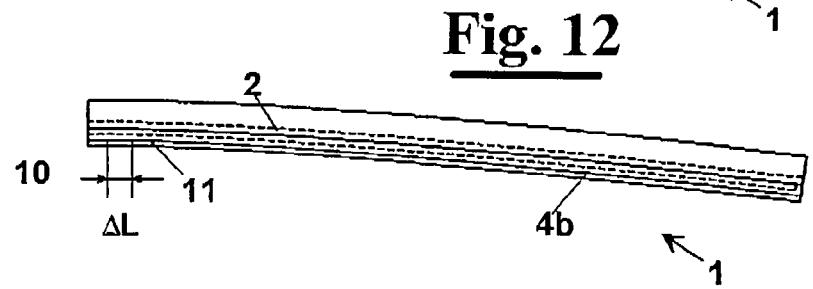

The alternative embodiment of the goniometric sensor 1 shown in FIGS. 11 and 12 comprises, instead, a channel 4b closed at the ends where a measured amount of an incompressible fluid is present, for example water, contacting a reference element 11. In this case, the bending of elongated element 2 causes the lengthening or shortening of the channel at line 15 and, therefore, a variation of the inner volume of channel 4b. This causes a variation of the distribution of the incompressible fluid in channel 4b and then a movement of reference element 11 of a, entity ΔL measurable with mechanical, optical, magnetic means or of other kind.

Alternatively, in channel 4b a compressible fluid can be inserted at a certain starting pressure Po. In this case the variation of the length of line 15, i.e. the variation then of the volume of channel 4b, causes a pressure variation ΔP that is detected and converted into a measure of the relative rotation of the two bodies 20 and 25.

In FIGS. 13 to 17 some possible applications are shown of goniometric sensor 1, as above described.

Figure 13:
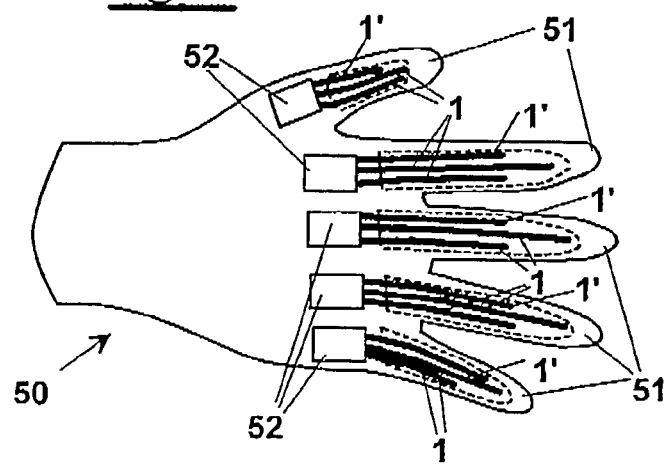
FIG. 13 shows a first possible application of the goniometric sensor of FIG. 1, in particular, a glove for goniometric measures or data glove.

In particular, in FIG. 13 a glove 50 is shown arranged with a plurality of goniometric sensors on each finger 51. This way, goniometric measures can be easily made necessary for different applications for example, in the field of virtual reality, or in the medical field for prosthesis designing or for making easier the rehabilitation of a limb subject to surgery causing the hand to follow predetermined movements. In the example, two goniometric sensors 1 are used for each finger 51 of the hand for measuring the flexo-extension of the phalanxs, and a goniometric sensor 1' is also used rotated of 90° about its own axis for measuring the abduction/adduction of the fingers 51 with respect to the hand. Each sensor has then an end constrained to the back of the hand in 52 and extends for at least one portion of the finger 51 same.

Figure 14:
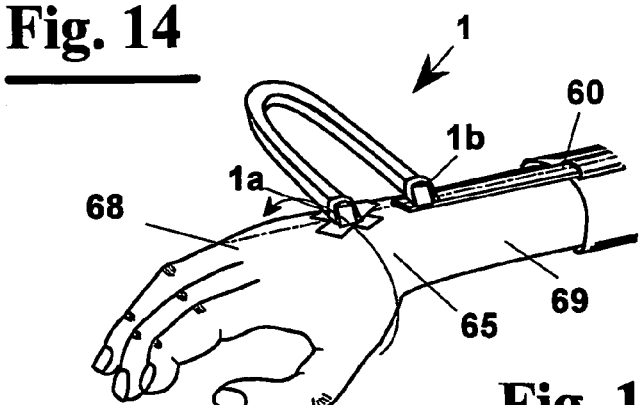
FIGS. 14 to 16 show a second possible application of the goniometric sensor of FIG. 1, in particular a device for measuring angular movements of a wrist.
Figure 15:
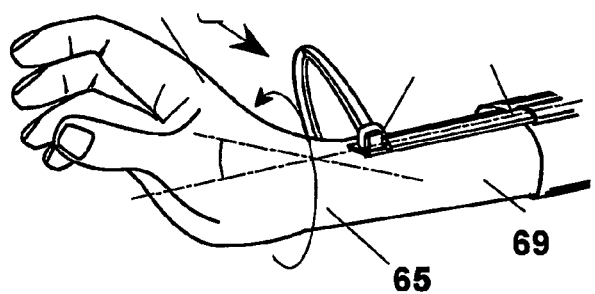
Figure 16:
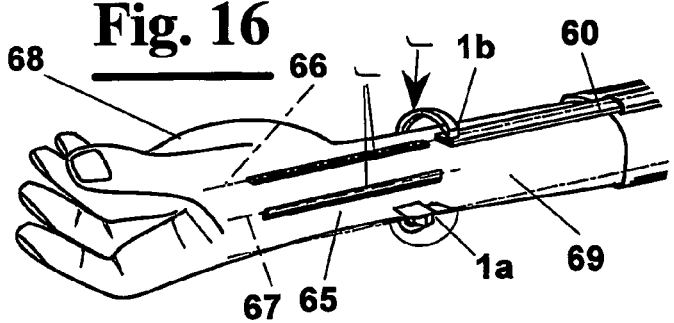

In FIGS. 14 to 16 a goniometric sensor 1 is shown used for measuring the rotation of a wrist 65 of a hand. In particular, the goniometric sensor 1 is arranged with an end 1a integral to the wrist 65 and with the other end 1b connected to a rod 60 constrained at the elbow and then the rotation is determined of the wrist 65 with respect to the elbow. Furthermore, two further sensors 1 are used at the wrist along two different directions 66 and 67 belonging to two planes orthogonal to each other that contain the axis of the forearm 69. The sensor arranged in direction 66, in particular, detects the flexo-extension of the hand 68 with respect to forearm, whereas the sensor in the direction 67 detects the ab/adduction of the hand 68 always with respect to forearm 69.

Figure 17:
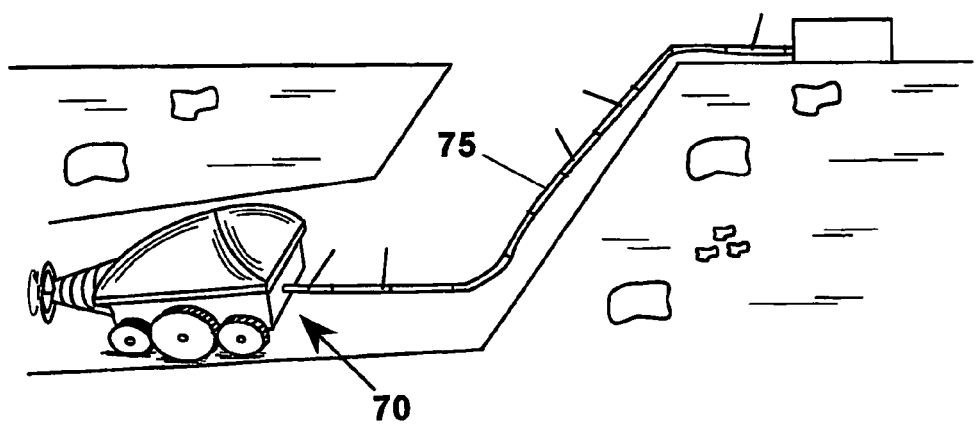
FIG. 17 shows a third possible application of the goniometric sensor of FIG. 1, in particular, an apparatus for tracking movements and localizing an object in movement.

Another particular application of the invention is shown in FIG. 17 and provides the use of a plurality of goniometric sensors $S_1 \ldots S_n$ arranged along a connecting cable 75 for monitoring movements and then localizing instantly "a tunnelling machine" 70 for explorations of the underground. In this case, the exact localisation of the object 70 is determined by integrating the measured data of the single goniometric sensors $S_1 \ldots S_n$. In particular, each goniometric sensor provides for each portion a couple of data of position, for example $\Delta x_i$, $\Delta y_i$, relative to the movement in that portion. therefore, adding the data relative to the single portions and knowing instantly the length of the cable 75 unwound allows to determine the spatial coordinates (x, y, z) of the object 70 monitored:

$$x = \sum_{i=n}^{i=0} \Delta x_i$$

$$y = \sum_{i=n}^{i=0} \Delta y_i$$

considering the single reference system rotated.

The foregoing description of a specific embodiment will so fully reveal the invention according to the conceptual point of view, so that others, by applying current knowledge, will be able to modify and/or adapt for various applications such an embodiment without further research and without parting from the invention, and it is therefore to be understood that such adaptations and modifications will have to be considered as equivalent to the specific embodiment. The means and the materials to realise the different functions described herein could have a different nature without, for this reason, departing from the field of the invention. It is to be understood that the phraseology or terminology employed herein is for the purpose of description and not of limitation.

The invention claimed is:

1. Method for measuring the relative rotation of a first object with respect to a second object comprising the steps of:
    arranging a flexible elongated element between said first and said second object and connecting ends of said flexible elongated element to said first and second objects, respectively, said element having a neutral axis, which does not change in length when bending, and defining at least one line spaced apart from said neutral axis and parallel to the neutral axis that extends from said first object to said second object, wherein said line is spaced apart from said neutral axis by a predetermined distance;
    rotating said first object relative to said second object;
    measuring a variation in length of said line during a relative rotation between said first and said second object, and calculating said relative rotation responsive to said length variation and said distance, said relative rotation being proportional to said length variation responsive to said distance independently of a shape of said line between said first and said second object.

2. Method according to claim 1, wherein said line is defined by a channel that runs along said line of said elongated flexible element, a medium being disposed in said channel transmitting a signal responsive to said length variation.

3. Method according to claim 2, wherein said medium is a fluid, said channel is tubular and closed at the ends, and said tubular channel contains a predetermined amount of a compressible fluid at a measured starting pressure, whereby said bending of the flexible elongated element causes a pressure variation of said fluid detected in said measuring step.

4. Method according to claim 2, wherein said medium is a fluid, said channel is tubular with a closed end and filled with a predetermined amount of and incompressible fluid, and a position reference element is arranged at an opposite end of the channel, bending of said flexible elongated element causing a variation of the distribution of the incompressible fluid in the tubular channel and a movement of the reference element that is detected by said means for measuring.

5. Method according to claim 2, wherein said medium suitable for transmitting is a cable connected to a first point of the channel, and wherein in said measuring step the movement of said cable at a second point of said channel is recorded.

6. Method according to claim 5, wherein said cable has an end connected to a first end of said channel and an opposite end freely moving, and in said measuring step the movement of the opposite end of the cable is recorded with respect to an opposite end of the channel.

7. Method according to claim 1, wherein in said measuring step means for measuring are employed selected from the group comprised of Hall effect sensors, optical sensors, magnetic induction sensors and piezoelectric sensors.

8. Method according to claim 1, wherein said bending of said flexible elongated element is carried out in a predetermined plane.

9. Glove for goniometric measures comprising at least one goniometric sensor including:
   means for arranging a flexible elongated element between a first and a second object, said element having a neutral axis, which does not change in length when bending, and defining at least one line spaced apart from said neutral axis and parallel to the neutral axis that extends from said first object to said second object; and
   means for measuring a variation in length of said line during a relative rotation between said first and said second object, said relative rotation being proportional to said length variation independently of a shape of said line between said first and said second object;
   said glove having at least one finger and a back side, said goniometric sensor being arranged with an end constrained to the back side of the glove and extending for at least one portion of one finger or located completely on the finger.

10. Glove according to claim 9, wherein at least two said goniometric sensors are used for each finger of the hand, including a first sensor measuring the flexo-extension of the phalanxs, and a second sensor rotated 90° about its own axis for measuring the abduction/adduction of the fingers with respect to the hand.

11. Device for measuring the rotation of a wrist comprising at least one goniometric sensor including:
   means for arranging a flexible elongated element between a first and a second object, said element having a neutral axis, which does not change in length when bending, and defining at least one line spaced apart from said neutral axis and parallel to the neutral axis that extends from said first object to said second object; and
   means for measuring a variation in length of said line during a relative rotation between said first and said second object, said relative rotation being proportional to said length variation independently of a shape of said line between said first and said second object;
   the at least one sensor arranged with an end integral to said wrist and with an opposite end constrained to a point of an arm that during rotation of said wrist remains substantially fixed, said device detecting the relative rotation of said wrist with respect to said second point.

12. Device for measuring the rotation of a wrist according to claim 11, comprising two said goniometric sensors at the wrist, which operate in two planes orthogonal to each other and that contain the axis of the forearm, for detecting respectively flexo-extension and ab/adduction of the hand with respect to forearm.

13. Device for localizing an object in the space by means of goniometric measurement, comprising a plurality of goniometric sensors, each of the sensors including:
   means for arranging a flexible elongated element between a first and a second object, said element having a neutral axis, which does not change in length when bending, and defining at least one line spaced apart from said neutral axis and parallel to the neutral axis that extends from said first object to said second object; and
   means for measuring a variation in length of said line during a relative rotation between said first and said second object, said relative rotation being proportional to said length variation independently of a shape of said line between said first and said second object;
   the sensors being arranged in series; and
   a computing unit for integrating data obtained by each of the goniometric sensors.

* * * * *